United States Patent [19]
Henley

[11] Patent Number: 5,415,629
[45] Date of Patent: May 16, 1995

[54] PROGRAMMABLE APPARATUS FOR THE TRANSDERMAL DELIVERY OF DRUGS AND METHOD

[76] Inventor: Julian L. Henley, 330 Orchard St., New Haven, Conn. 06511-4417

[21] Appl. No.: 122,717

[22] Filed: Sep. 15, 1993

[51] Int. Cl.⁶ .............................................. A61N 1/30
[52] U.S. Cl. ..................................................... 604/20
[58] Field of Search ............................ 604/20, 49, 21; 607/149-152; 128/639, 644, 783, 798, 799, 802, 803

[56] References Cited

U.S. PATENT DOCUMENTS

| | | | |
|---|---|---|---|
| 1,967,927 | 7/1934 | Deustch | 604/20 |
| 4,301,794 | 11/1981 | Tapper | 604/20 |
| 4,474,570 | 10/1984 | Ariusa et al. | 604/20 |
| 4,786,278 | 11/1988 | Masaki | 604/20 |
| 4,808,152 | 2/1989 | Sibalis | 604/20 |
| 4,820,263 | 4/1989 | Spevak et al. | 604/20 |
| 4,865,582 | 9/1989 | Sibalis | 604/20 |
| 4,931,046 | 6/1990 | Newman | 604/20 |
| 4,942,883 | 7/1990 | Newman | 604/20 |
| 5,006,108 | 4/1991 | LaPrade | 604/20 |
| 5,047,007 | 9/1991 | McNichols et al. | 604/20 |
| 5,053,001 | 10/1991 | Reller et al. | 604/20 |
| 5,135,479 | 8/1992 | Sibalis et al. | 604/20 |
| 5,160,316 | 11/1992 | Henley | 604/20 |
| 5,254,081 | 10/1993 | Maurer et al. | 604/20 |

FOREIGN PATENT DOCUMENTS

| | | | |
|---|---|---|---|
| 0230749 | 8/1987 | Japan | 604/20 |
| 8571 | 8/1990 | WIPO | 604/20 |
| 3790 | 3/1993 | WIPO | 604/20 |

Primary Examiner—John D. Yasko
Assistant Examiner—Manuel Mendez
Attorney, Agent, or Firm—Michael G. Petit

[57] ABSTRACT

An apparatus is described for the programmable iontophoretic or iontophoretic-ultrasonic (ionosonic) transdermal delivery of medication across the skin or other biological membrane. In one embodiment, the programmable apparatus controls the depth of penetration of a medicament into the skin. In another embodiment the programmed delivery of medicament is accompanied by an electrical stimulus for treating substance abuse. The apparatus can be adapted for large dermal area application or for a smaller area of application, depending on the choice of specific electrode employed. In a preferred embodiment the apparatus comprises a multichannel iontophoretic applicator electrode. Multiple piezoelectric elements are mounted on the iontophoretic electrode. The combination of ultrasonic vibration and iontophoresis improves the penetration of medicament in contact with the skin or mucous membrane underlying the electrode which can be programmably controlled by a CPU through the use of a EPROM. A wearable embodiment of an ionosonic or iontophoretic drug delivery system employing programmability may be used to produce response conditioning useful for the outpatient treatment of obesity, nicotine detoxification, and narcotic addiction detoxification.

12 Claims, 3 Drawing Sheets

PROGRAMMABLE APPARATUS FOR THE TRANSDERMAL DELIVERY OF DRUGS AND METHOD

BACKGROUND OF THE INVENTION

1. Field of the Invention

This invention relates generally to the transdermal delivery of medicament and, more specifically, to a wearable programmable apparatus for the iontophoretic and/or ionosonic delivery of medication across the skin or other biological tissue for the prevention of a disease such as thrombosis and the management and treatment of medical conditions such as substance abuse.

2. Reference to Copending Patent Application

Reference is made herein to copending application Ser. No. 08/044,586 filed 04/07/93 entitled: Ionosonic Drug Delivery Apparatus, by the present inventor.

3. Prior Art

Iontophoresis has existed for several centuries as a means for applying medication locally through a patient's skin and for delivering medicaments to the eyes and ears. The application of an electric field to the skin is known to greatly enhance the skin's permeability to various ionic agents. The use of iontophoretic techniques has obviated the need for hypodermic injection of certain medicaments, thereby eliminating the concomitant problems of trauma, pain and risk of infection to the patient.

Iontophores is involves the application of an electromotive force to drive or repel oppositely charged ions through the dermal layers into the area to be treated; either into the surrounding tissues for localized treatment or into the circulatory system for systemic treatment. Positively charged ions are driven into the skin at the anode while negatively charged ions are driven into the skin at the cathode. Studies have shown increased skin penetration of drugs at anodic or cathodic electrodes regardless of the predominant molecular ionic charge. This effect is mediated by polarization and osmotic effects. Regardless of the electrical charge on the medicament employed, two electrodes are used in conjunction with the patient's skin to form a closed circuit to promote the penetration or absorption of the medicament through the skin underlying the working electrode.

One readily observed benefit of transdermal iontophoretic drug delivery is the increased efficacy of the drugs delivered in this fashion. U.S. Pat. No. 5,160,316, to the instant inventor, incorporated herein by reference, describes the use of a multichannel dispersive electrode. Each channel is driven by separate electronic circuits to assure wide dispersion and enhanced penetration of medicament. Such wide field electrodes not only can cover a wide area of body without succumbing to "tunneling effects" but provide sufficient skin penetration to function as a systemic drug delivery system. A co-pending patent application by the present inventor describes a user-friendly iontophoretic system to deliver nicotine as a means for helping people quit smoking or, alternatively, to provide established smokers with a noncarcinogenic smokeless cigarette. Another co-pending patent application describes the novel utilization of an integrated system of multichannel iontophoretic drivers combined with ultrasonic piezoelectric elements to achieve greater skin penetration of transdermal deliverable drugs and even larger peptide molecules such as insulin.

Transdermal delivery of medicament offers a new and potentially powerful tool for the treatment of substance abuse and dependency problems. Substance abuse/dependency has in recent years emerged as a significant problem for our society, not to mention the suffering and health of substance-dependent individuals and their families who are substance dependent. Substances that are commonly abused and constitute a significant costly impact on our society are; FOOD, TOBACCO, ALCOHOL, AND DRUGS. Although substance dependency is a complex and multifactorial entity beyond the scope of this discussion, recent studies have identified some common factors. Each substance abuse situation creates an altered mental state, and temporarily satisfies an inner need. Many substance dependent people desire and struggle to be free of their dependency.

Current treatments employ a combination of supportive social and psychological treatment in conjunction with pharmacological intervention that either blocks the effect of, or substitutes for, the substance being abused. Pharmacological intervention has shown itself to be of increasing value in the management of substance abuse. Studies are identifying drugs and peptides which are active in appetite suppression for weight loss treatment. Studies are showing increasing efficacy of medications in the detoxification and perhaps ultimate treatment of drug dependency. Current management has been limited by patient compliance and difficulties associated with outpatient management of substance abusers.

In view of the foregoing problems with current management and treatment regimens, it is desirable to provide a method for helping a patient conquer his/her addiction while allowing the patient to exercise significant control over their own treatment. An intelligent, programmable transcutaneous drug delivery system that is portable, can be worn for extended periods of time, can be dose limited, deliver a substance that blocks or substitutes for the dependency in a pre-programmed manner, and can deliver additional medication rapidly under patient control for special situations of greater need, would provide a powerful adjunct to the management of people who are substance dependent.

SUMMARY OF THE INVENTION

The invention employs needleless programmable transcutaneous drug delivery system such as a multichannel iontophoretic electrode array formed into a flexible sheet. Such a flexible sheet may be small enough to be worn around the wrist or cover a large part of the body for institutional use. Remote power and control circuits may be joined to the flexible sheet by ribbon cabling for institutional treatments requiring higher power densities, higher dosing or treatment of specific areas such as burns, infection or special anatomic areas such as oral gums. Such a wide-field high-dosing embodiment of the device is useful for the management of institutionalized drug detoxification patients requiring a high-dose detoxification regimen on a programmable basis. Such a system can lower the costs of repeated dosing and injections requiring skilled nursing care. Such a system would offer great improvement in management of hospitalized post operative or cancer pain patients. Studies have shown that multiple preemptive pain dosing with some patient control of supplemental dosing greatly improves the efficacy of pain control with less total narcotic dosing.

It is a primary object of the invention to provide a device and method for the management and treatment of substance abuse.

It is another object of the inventor to provide a device useful for the prevention of a medical disease such as thrombosis.

It is yet another object of the present invention to provide an iontophoretic and/or ionosonic medicament applicator wherein the neutral electrode array and active electrode array are integrated into a band-type of device to be worn about a portion of the body providing for comfort and electrical contact with skin.

It is another object of the invention to provide a system for painless, controlled and safe delivery of drugs, peptide and other substances through the skin or mucous membrane.

It is an object of the present invention to provide an iontophoretic or ionosonic medicament applicator which improves the efficacy of topical agents and reduces the risk of harmful side effects that may occur with oral systemic treatment techniques.

It is yet another object of the present invention to provide a disposable iontophoretic or ionosonic medicament applicator which conducts the electrical current to the tissue through the solution in which the medicament is dissolved.

It is still object of the present invention that the improved disposable iontophoretic medicament applicator has a low production cost, is safe to use and increases the efficacy of the medicament employed.

It is another primary object of the invention to provide an iontophoretic or ionosonic medicament applicator which delivers a programmable dose of medicament through the skin.

It is yet another object of the invention to provide a medicament applicator which controls the depth of penetration of a medicament into the skin.

It is another object of the invention to provide a programmable transdermal medicament delivery apparatus in which the programmable delivery of medicament be accompanied by a physical stimulus.

These and other objects, features and advantages are obtained by the improved iontophoretic or ionosonic medicament applicator of the present invention. Various embodiments of the invention can be used to treat large dermal areas, localized areas or small and difficult to reach areas, and even include a programmable "watch band" type of a systemic drug delivery system useful for treating outpatients.

It yet another and unique feature of this apparatus that a manually controlled supplemental dose of medicament can be delivered. Such manual control empowers the patient to control his or her own craving at moment of need by supplying a limited but supplemental dose of medicament such as nicotine or appetite suppressant when needed.

It yet another unique feature of this apparatus that the activation of the apparatus (when the apparatus is actively moving medication across the skin) causes a mild tingling sensation to be experienced. This is implemented by means of a skin-contacting electrode modulated with a square, rectangular or oscillating current in the range of 10–300 HZ and 10–40 volts. The activation of this stimulant electrode is under the programmable CPU control. This tingling sensation associated with delivery of transdermal nicotine or appetite suppressant reinforces a psychological link. This feature may play an important role in the process of gradually weaning a patient from substance dependency. The patient receives an ever-decreasing dose of nicotine until eventually the tingling sensation alone facilitates the change in mental state that will help the patient blunt his/her craving. The associated tingling sensation may ultimately suffice to resolve the momentary cravings for food, cigarettes, or other addictive substances.

BRIEF DESCRIPTION OF THE DRAWINGS

The objects, features and advantages of the invention will become apparent upon consideration of the following detailed disclosure of the invention, especially when it is taken in conjunction with the accompanying drawings wherein.

GENERAL DESCRIPTION OF THE INVENTION

Figure 1:
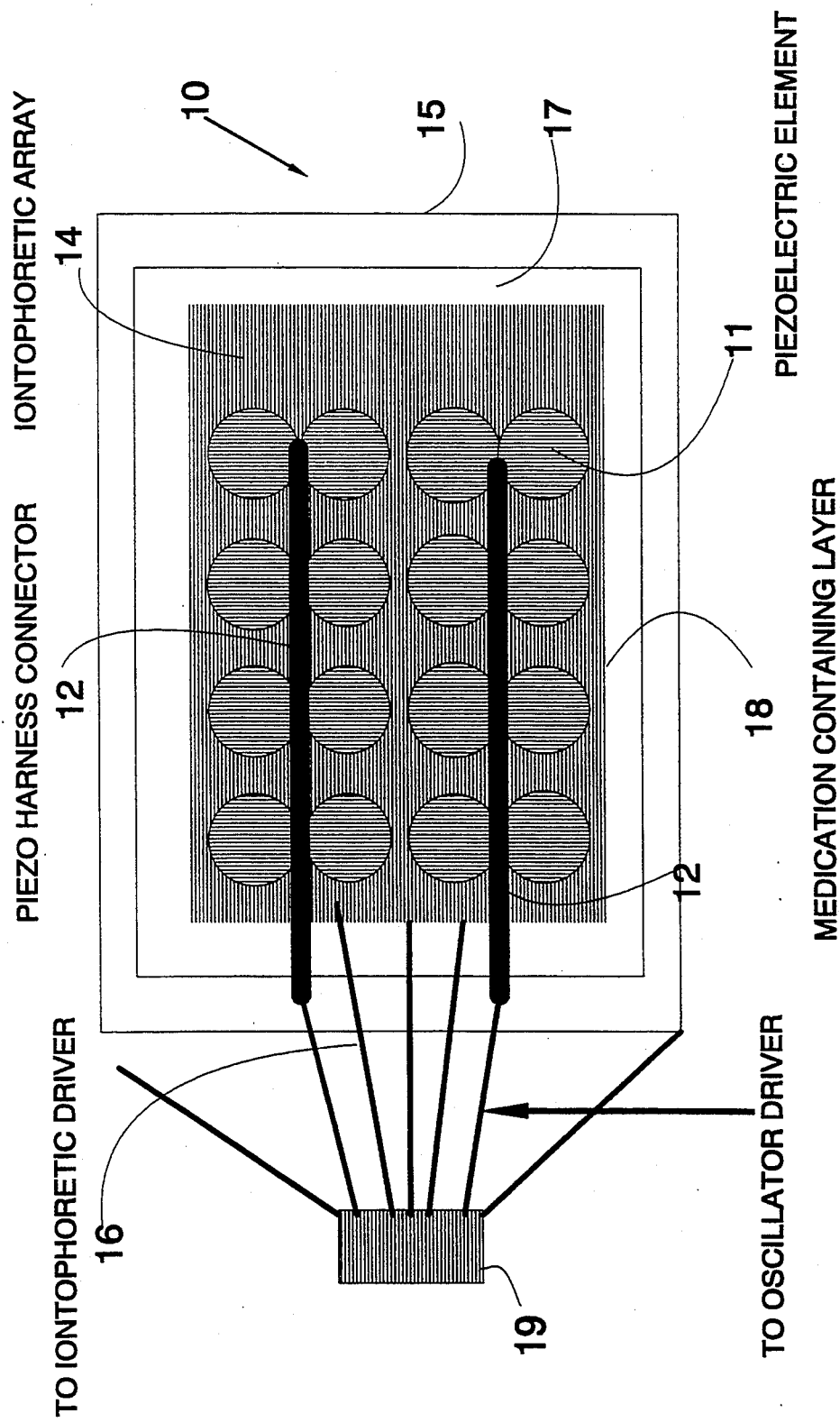
FIG. 1 is a top plan view of one embodiment of the improved multichannel iontophoretic applicator combined with several of the plurality of ultrasonic elements which can be used to treat large dermal areas.

This invention provides a portable, programmable, battery-powered, wearable apparatus composed of driver electronics described in prior U.S. Pat. No. 5,160,316, (incorporated herein in its entirety by reference) combined with a neutral and active application electrode in contact with a medication reservoir. The apparatus may be used as a system to help people manage their substance dependency and addiction. Such a system can be programmed to transcutaneously deliver medication in a variable time domain fashion and provide additional manual override capability for direct patient control. For example, an appetite suppressant (i.e.: cholecystokinin) can be released in accordance with a timed meal schedule yet have the capability to allow the overweight patient to release additional suppressant in time of need. Another example of the utility of this system is for the release of nicotine on a preprogrammed basis, permitting the additional release of nicotine when the patient quitting smoking faces an unusual craving situation. The total daily dosing can be device limited yet delivered in an intelligent, responsive dynamic manner to improve efficacy while decreasing the total daily dose when compared to current passive delivery systems such as the nicotine patch.

These problems are solved in the design of the present invention by placing an improved iontophoretic medicament applicator under programmable control and, in one embodiment, combining this iontophoretic dispersion electrode with ultrasonic enhancement of penetration. The instant inventor has discovered that combining a multichannel iontophoretic electrode with ultrasonic enhancement greatly improves the skin penetration and transdermal movement of larger molecules such as insulin or other peptides. Ultrasound applied to the skin has been shown to enhance skin penetration by (a) disrupting the protective keratin layer; and (b) forming micro-droplets that can readily be charged. A transdermal delivery system combining ultrasound and iontophoresis may be adapted to incorporate a CPU and EPROM for both dosing and depth of penetration programmability. Such an apparatus, accompanied by a supplementary manual dosing capability and sensory stimulation to promote conditioning behavior change may be helpful in substance abuse detoxification. Such an apparatus is primarily controlled by a programmable CPU and EPROM system with a patient controlled manual supplement to deliver substances active in the treatment of substance abuse problems.

Although numerous commercially available CPU's and EPROM's can be utilized, a preferred configuration uses the Intel® 80C51 CMOS CPU that has great flexibility with low voltage and low power requirements. This CPU incorporates a limited EPROM capability. When extended dosing programmability is required, additional EPROM capacity can readily be supplied by linking a 27C256 CMOS EPROM supplied by numerous manufactures. Such a system, which incorporates the aforementioned dosing programmability with respect to the time of day and amount of dosing opens up a new realm of possibilities in the clinical management of pharmaceutical appetite suppression. In a similar manner such an apparatus can be worn for extended periods of time and facilitate outpatient management of numerous substance abuse situations. Such apparatus can be used to deliver appetite suppressants (cholecystokinin), nicotine, Valium® and Naloxone® or other medications approved for the management of drug or substance dependency.

The apparatus described herein can deliver heparin (peptide) to patients requiring anticoagulation to prevent strokes or for embolization prophylaxis following heart valve replacement. At present most outpatient anticoagulation is accomplished with coumadin, a long acting anticoagulant. In the event that such a patient requires surgery or is bleeding acutely, complications often occur because it takes 24–36 hours to reverse the effects of coumadin. For perioperative anticoagulation to prevent deep vein thrombosis and other clotting complications, Heparin is used but needs to be administered via injection frequently and is not used for long term outpatient anticoagulation. Heparin is superior to Coumadin because it is short acting and its effects are readily reversed when administration is stopped. The apparatus described herein lends itself to this important medical application. When Heparin can be driven through the skin using a programmable ionosonic, wearable apparatus programmed with the suitable dosing strategy custom designed for the patient.

Fentanyl®, a short acting narcotic, is currently commercially available as a passive patch for pain management. Combining such a passive transdermal delivery system with the programmable, wearable ionosonic or iontophoretic drug delivery apparatus of the present invention will greatly improve the current medical management of pain, drug/substance detoxification, and many other illnesses currently managed by injections and repeated dosing of drugs. Such an apparatus provides a greatly improved method of drug delivery over the current timed release technology. Such technology incorporated into a wearable apparatus may ultimately replace birth control pills and require less dosing, produce less side effects, and be programmed to release ovulation suppressing hormones only at the critical times. Although many of the foregoing applications presented herein are possibilities for future technologies, the present invention addresses a currently critical social problem by providing an effective, wearable, intelligent apparatus and method for the management of drug and substance abuse addiction.

One of the preferred embodiments may be worn like a wide watch band with the electronics and power source mounted thereon in a manner resembling to a large watch. The inner surface of the band contains the active and grounding multichannel dispersive electrode. The ultrasonic elements are placed within this band in close proximity to each electrode channel. The inner surface may be an adhesive, an open cell material or a peptide-impregnated hydrogel or other similar matrix. This inner band surface containing the medicament is preferably disposable and contains a specified amount of desired medicament such as insulin.

In another non-programmable embodiment, the apparatus of the present invention readily lends itself to the systemic delivery of medication under the control of a physiological sensor connected to the delivery system in a biofeedback configuration. Thus, the delivery of nitroglycerin based on heart rate sensing; the delivery of blood pressure medication based on blood pressure sensing; and the transdermal delivery of insulin by means of either the iontophoretic or iontophoretic-ultrasonic system regulated and controlled by a similarly noninvasive glucose sensor are all feasible applications for the invention. Sensors for heart rate, sweating, and blood pressure are readily available and can be integrated with this system to further modify the transcutaneous delivery of medication used to treat a particular substance dependency.

Activation of the apparatus (i.e.: when the apparatus is actively moving medication across the skin ) preferably causes a mild tingling sensation or other such stimulus to be experienced by the patient. The tingling sensation is produced by means of a contact electrode modulated with a square, rectangular or oscillating current in the range of 10–300 HZ and 10–40 volts. The activation of this stimulant electrode is under the control of a drug, for example, programmable CPU. Because the tingling sensation is associated with the delivery of transdermal nicotine or appetite suppressant, it will reinforce a psychological link between satiety and the tingling sensation. It is believed that this feature will play an important role in the process of gradually weaning patients from substance dependency. The patient will receive ever decreasing doses of nicotine yet the tingling sensation alone may facilitate the mental state change that will help the patient blunt his/her craving. The associated tingling sensation may ultimately suffice to resolve the momentary cravings for food, cigarettes, or other addictive substances.

The programmability feature of this invention offers significant advantages for divergent applications. As an example, when a situation exists where it is of paramount importance to achieve increased saturation of the dermal and subdermal layers with a given pharmaceutical, yet it is desirable to minimize systemic absorption, a unique programmability technique can be applied. The iontophoretic and/or ionosonic drives can be utilized in a pulse fashion wherein for a programmable duration of time the pharmaceutical is driven into the dermis until saturation is achieved. Once the dermis is saturated, a programmed polarity reversal of the driving electrode occurs to stabilize and contain the saturating medicament within the dermis itself while minimizing the flow-through of medicament to the subdermal plexus and the vascular trees.

As an example of the value of controlling the depth penetration of a transdermally deliverable medicament, it would be of significant benefit for the clinical application of Minoxidil for stimulation of hair growth. Since Minoxidil is systemically toxic and its greatest benefit is derived from saturation into the dermis, such penetration control can significantly reduce side effects and improve efficacy. Iontophoresis, as such, produces an electrical sieving effect through the hair follicles where it has a natural advantage of increasing the Minoxidil concentration within the hair root where Minoxidil's pharmacological activity produces the greatest effect. The flexibility of programmability can be utilized to give a positive directional pulse followed after pre-programmed first duration of time, by a polarity reversal which occurs for a second pre-programmed time duration. Such programmable control over pulsing and polarity reversal gives the iontophoretic ionosonic device enhanced control over the depth of penetration of medicament and differential saturation of the dermis. The duration of these pulses is determined by the electrical conductivity of the skin, the thickness of the dermis and the desired area of application.

Such pulsing and polarity reversal programmability is readily implemented into the present apparatus. Yet another example of the clinical application of the present apparatus is in the treatment of fungal infections of nails and skin such as tinea capitis. There are many systemically toxic pharmaceutical agents which interfere with fungal metabolism preventing replication. It would be highly desirable to avoid systemic toxicity by achieving clinically high concentration within the dermis where the fungal infection is proliferating.

DETAILED DESCRIPTION OF THE PREFERRED EMBODIMENT

An ionosonic applicator working electrode, generally indicated at the numeral 10, is shown in FIG. 1. The ionosonic applicator electrode has been described in detail in by the present inventor in copending U.S. patent application Ser. No. 08/044,586 filed 04/07/93. The applicator electrode 10 forms a closed circuit through the patient's body when current is applied which promotes the penetration or absorption of an ionic medicament contained in a layer 18 of the applicator electrode 10. The polarity of the working electrode 10 is selected based upon the polarity of the medicament to be administered. The working or applicator electrode 10 preferably comprises a flexible sheet forming a conductive matrix 15 having a current distributing conductive layer on the skin contacting surface 17 thereof, such as a metallic foil, a conductive rubber or resin film, carbon film or other conductive coating or electrodispersive material. The conductive matrix 15 is flexible so that it may be contoured to the body area on which it is placed and still cover a relatively wide area. The conductive matrix 15 has a medicament-carrying layer 18 attached to it, such as by an adhesive. The medicament carrying layer 18 is preferably formed from a porous material about ¼ of an inch thick which can be a honeycombed sponge-like open-celled material with cells preferably vertical to the skin to minimize cross flow or lateral dispersion of the medicament. The grounding electrode (not shown) employed with the multichannel electrode 14 must cover an area similar in size to the area covered by the multichannel electrode 14.

A ribbon connector (not shown) connects an electrical power source (not shown) to the multichannel electrode 14 and, in addition, delivers the electrical current by means of the multiconnectors 19 to the lead wires 16 (only some of which are shown) that form the individual electrically conductive channels in the conductive matrix 15. Since the construction material used to fabricate the conductive matrix 15 is flexible, the working electrode 10 may be folded over a rigid supporting substrate above the connectors 19 to insure that a good electrical connection is made with the ribbon connector. Each channel in the multichannel electrode or iontophoretic array 14 preferably carries no more than 1 milliamp of current. The amount of current that flows to each channel is controlled by the control circuit (shown in FIG. 3) to prevent a tunneling effect from occurring. This prevents the flow of current along the path of least resistance through a lesion or skin rupture, for example, which can result in a burn to the patient at that location. The multichannel electrode 14 can employ a circuit pattern etched such as by laser or photoetching onto, for example, a metal coated Mylar® plastic sheet with each channel isolated to facilitate dispersion over a broad surface area.

Each channel formed by the lead wires 16 can be electrically driven simultaneously or in a sequential multiplex manner. The use of simultaneous or parallel electrical current to each lead wire 16 in the array 14 would be employed, for example, in the application of medicament to burns where a wide area of dispersion is required. The ionosonic applicator greatly improves the skin penetration by the medicament to actively deliver the medicament to either a wide regional area or to a specific lesion.

Ultrasonic elements 11 made of piezoelectric crystal elements are mounted on this flexible working electrode 10 by means of a suitable adhesive such as Silastic TM brand of silicone adhesive. Driving oscillator connections 12 to the crystals can be photoetched onto a polymer sheet (eg; metalized Mylar TM) with perforations on the sheet which facilitate mounting of the ultrasonic elements. The electrode is effective for moving insulin across skin, as well as antibiotics, antifungal, anti-inflammatory, blood pressure medication and cardiotropic drugs; either as direct drive, programmably driven or, more elegantly, driven in response to a biofeedback control configuration. It is also effective in the treatment of wide-field dermatological conditions, such as eczema, psoriasis and acne. It is also effective for ionic retention of skin hydrating media to facilitate skin hydration in cosmetic applications and in dermal exfoliation to drive medication into the skin in order to inflame the skin and cause the peeling of the external skin layer to stimulate reformation of collagen and collagen growth factors. The ionosonic applicator may also prove useful for driving Minoxidil or related compounds into the scalp to enhance hair growth and/or ameliorate baldness. The ionosonic applicator can be used to drive anticoagulants such as Heparin or enoxaparin, a lower molecular weight (4,000–6,500 D) peptide sold under the tradename lovenox ® by Rhone-Poulenc Rorer, to provide outpatients with a safer and better controlled long term anticoagulant.

The ultrasonic elements 11 can be piezo-electric crystals, ceramics or distributed segments of Kynar TM PVDF piezo film.

The open-celled sponge-like material in the medicament carrying layer 18 should be inert to the medicament or treatment agent being employed, as well as being noncorrosive and stable. Suitable materials include plastic pads, such as polyethylene, cellulosic material such as paper or cotton, porous ceramics, open-celled porous PTFE, other inert plastics, and open-celled silicone rubber, preferably with vertically aligned cells or tubes for containing and dispensing medicament.

Figure 2:
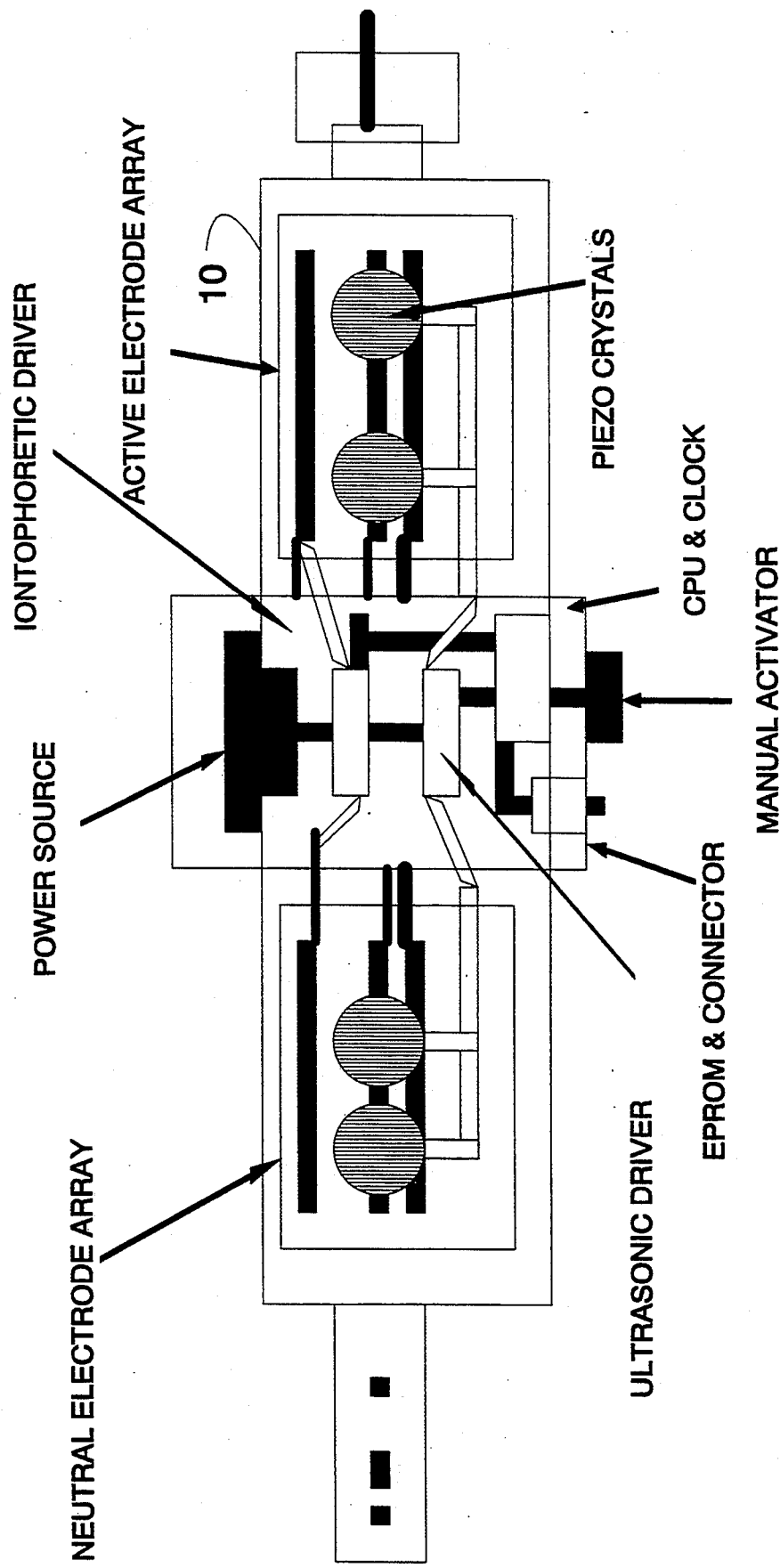
FIG. 2 is a top, somewhat schematic, plan view of a miniaturized embodiment of the improved iontophoretic-ultrasonic delivery system combined with a sensor (eg; tissue glucose, blood pressure, or heart rate sensors) to form a biofeedback system for intelligent and controlled drug delivery. This system can be worn as a "watch band" on an extremity.
Figure 3:
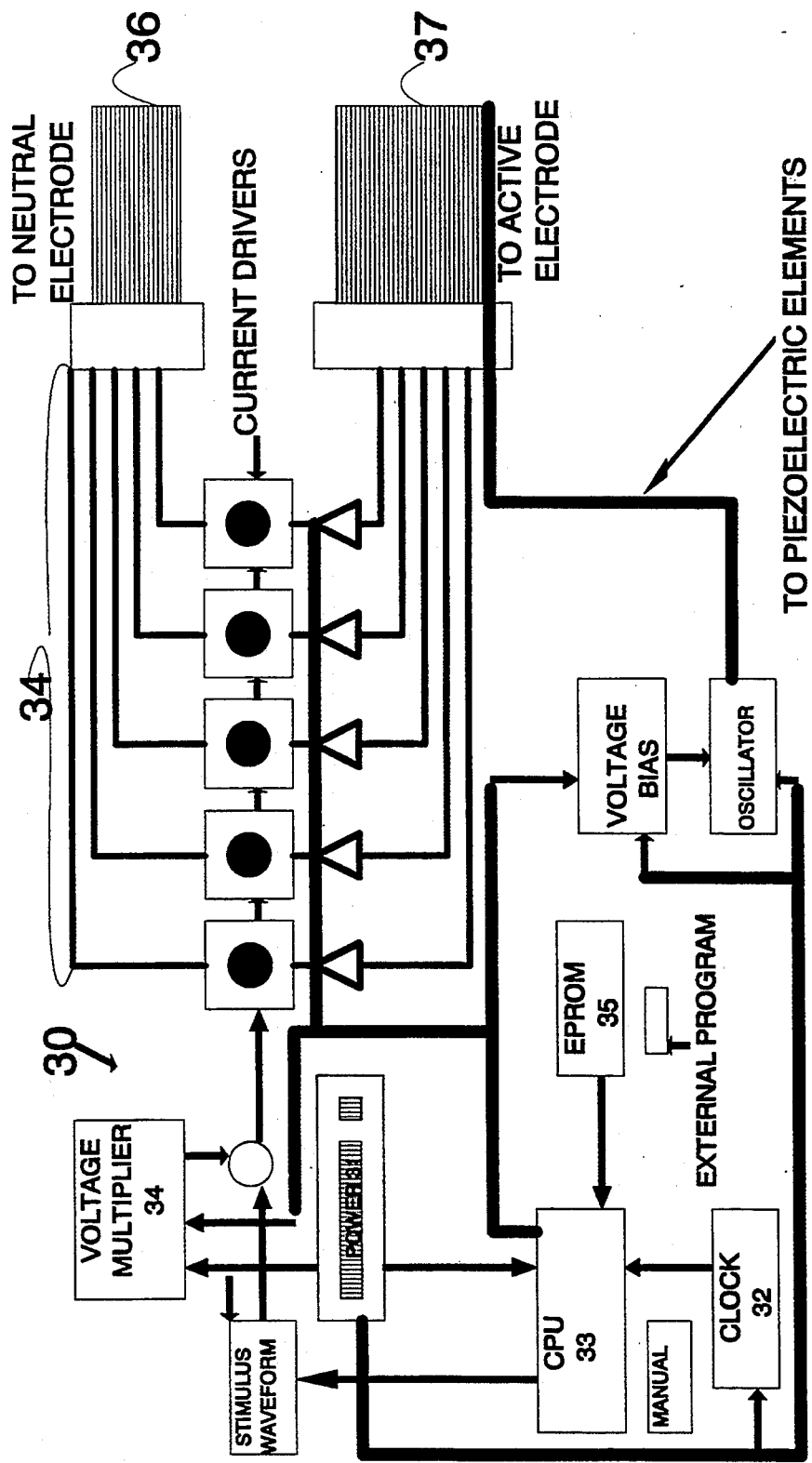
FIG. 3 is a block circuit diagram of the iontophoretic-ultrasonic (ionosonic) medicament applicator's electrical control circuit used in conjunction with above applicators either as a separate power and control unit or integrated into a single unit if market demand justifies the costs of such miniaturization.

FIG. 3 shows a block circuit diagram of a electrical control circuit suitable for use with the ionosonic applicator of FIG. 1 and the miniaturized ionosonic applicator diagrammed in FIG. 2. The neutral and working electrodes have been omitted for clarity. The control circuit, generally indicated at 30, may be either integrated with the electrode, as shown in FIG. 2, or housed separately to drive the applicator electrode as shown in FIG. 1. The control circuit 30 is equipped with a power source 31 which may be either a battery or an isolated wall source.

The control circuit 30 is provided with a clock-operated timer switch 32 to preset the length of iontophoretic treatment mediated by the integral CPU 33. Once the length of time has been selected, a voltage multiplier 34 is utilized to provide the current to iontophoretically drive the medicament into the patient's skin. The current is set by the CPU 33 which is under control of the EPROM 35 and administered until the end of the treatment period. When the clock 32 signals the end of the treatment period, the electrical current to the working electrode 10 (not shown in FIG. 3) is gradually terminated by a ramping down of the current to the patient to avoid abrupt change. Ribbon cable (36 and 37) provides a flexible connection to the multichannel neutral and working electrodes respectively, as well as delivering oscillator power for the piezoelectric crystals 11 mounted on the applicator electrode 10. Internal circuit board controls allow for frequency adjustment, adjustment of maximum current per iontophoretic channel (not to exceed 0.6 to 1.2 ma range), and an internal control which will shut down any iontophoretic channel electrically performing outside a "normal" range of encountered biological impedance.

An isolated current loop generator 34 is employed to feed current to the individual channels in the multichannel electrode via the plurality of individual current loops. Each current loop drives one band or channel in the multichannel electrode. It has been found that 0.6 milliamps current flowing to each channel used within a wide field dispersion grounding electrode, such as that shown in FIG. 1, provides a safe level for operating the iontophoretic device. This level of current avoids the tunnelling effect of current flowing along the path of least resistance and concentrating in, for example, a lesion or skin rupture, resulting in a burn to the patient. This permits current to be distributed over the large area of the multichannel electrode to drive medicament through a patient's skin over a relatively large dermal area. Depending upon the electrode configuration, this current level can vary from about 0.1 to about 1.2 milliamps. The novel introduction of distributed ultrasonic piezoelectric elements combined with the iontophoretic multi electrodes described above greatly enhances the rate of penetration of many molecules. The use of an ionosonic applicator renders the transdermal administration of insulin feasible.

While the invention has been described above with references to specific embodiments thereof, it is apparent that many changes, modifications and variations in the materials, arrangements of parts and steps can be made without departing from the inventive concept disclosed herein. This is particularly true of medical condition which may be successfully treated a managed using the apparatus of the present invention. For example, in employing the multichannel iontophoretic electrode of the present invention, it is possible to employ a biofeedback control to dispense, for example, more cardiovascular medication during periods of increased physiological demands, such as during exercise or an angina attack. This can be accomplished by linking the penetration of nitroglycerine with heart rate; the physiological indicator of oxygen demand by the heart. In the latter instance, a sensor electrode would measure the increased demand and signal the controller 30 to stimulate more delivery of the transdermal medication, in this case, nitroglycerine (commercially available under the trade name Nitropaste ®). This type of a biofeedback coupled with ionosonic application provides an active system for percutaneous nitroglycerine delivery which is an improvement over existing passive percutaneous delivery systems. The present invention creates a further improvement in transdermal penetration of medicament over prior purely iontophoretic or ionosonic delivery systems by introducing programmability to control the iontophoretic penetration of medicament.

Alternate applications also exist in hormonal therapy, for example in the administration of insulin or steroids based on blood sugar levels and diurnal cycles, as appropriate. The large area multichannel electrode shown in FIG. 1 or FIG. 2 can also be adapted for use in dental anaesthesia in the form of a bite block, burn treatment and for the treatment of baldness, such as by the transdermal administration of Minoxidil. Additionally, a conductive gel can also be used to impregnate the porous medicament carrying medium to increase the physical stability and the tissue adhering characteristics of the electrode. Or, a medicament may be dispersed in a conductive gel and a layer of the gel providing the medicament carrying layer. Also, as mentioned earlier, the wearable ionosonic delivery system of the present invention may be used to deliver Heparin or Enoxaparin to prevent thrombosis. Enoxaparin has a lower molecular weight (4,000–6,500) than heparin (12,000–15,000) facilitating its ionosonic transport across the skin.

Accordingly, the spirit and broad scope of the appended claims is intended to embrace all such changes, modifications and variations that may occur to one of skill in the art upon a reading of the disclosure. All patent applications, patents and other publications cited herein are incorporated by reference in their entirety.

I claim:

1. An iontophoretic transdermal medicament applicator comprising in combination:
   (a) a medicament carrying layer;
   (b) an electrically conductive means electrically connected to said medicament carrying layer, sand electrically conductive means further comprising a plurality of electrode channels wherein each electrode channel is independently electrically driven to iontophoretically drive a medicament from said medicament carrying layer into the skin of a patient;

(c) means for applying a driving voltage to said electrode channels;

(d) programmable means for varying said driving voltage with respect to amplitude, polarity and time and wherein said programmable means for varying said polarity of said driving voltage is operable for controlling the depth of penetration of a medicament into the skin.

2. The iontophoretic medicament applicator of claim 1 wherein said electrically conductive means further comprises a flexible sheet of substantially electrically non-conductive material with electrically conductive electrode channels supported thereon.

3. The iontophoretic medicament applicator of claim 2 wherein the electrically conductive means comprises a layer of electrically conductive material laminated to a sheet of electrically non-conducting material and wherein a conducting circuit pattern is etched into said conducting layer.

4. The iontophoretic medicament applicator of claim 1 wherein the medicament carrying layer comprises a porous material.

5. The iontophoretic medicament applicator of claim 1 wherein the medicament carrying layer comprises a conductive gel.

6. The iontophoretic medicament applicator of claim 4 wherein said porous material comprises a sponge-like material with vertical cells.

7. The iontophoretic medicament applicator of claim 4 wherein the porous medicament carrying layer comprises an open-celled material selected from the group consisting of polyethylene, paper, cotton, ceramic, silicone rubber and polytetrafluoroethylene.

8. The iontophoretic medicament applicator of claim 1 wherein the polarity, duration and amplitude of said driving voltage applied to said multichannel electrodes by said means for applying said driving voltage are programmable.

9. The ionotophoretic medicament applicator of claim 1 further comprising:

(a) non-programmable means for dosing control; and (b) second programmable means for measuring the total dosage of said medicament delivered to said patient by said programmable means and non-programmable means to assure that the total daily dose is not exceeded.

10. The iontophoretic medicament applicator of claim 1 further comprising means for the delivery of an electrically generated stimulus to the skin to create a tingling sensation contemporaneously with the delivery of said medicament into said skin of said patient.

11. The iontophoretic medicament applicator of claim 9 wherein said medicament is an anticoagulant.

12. A method for controlling the depth of penetration of an iontophoretically administered medicament into the skin of a patient comprising the steps of:

(a) applying a programmable, pulsed voltage having a first polarity to an iontophoresis electrode, said iontohoresis electrode being in electrical connection with a skin-contacting medicament-contaning layer for a first period of time of sufficient duration to drive at least a portion of said medicament from said medicament-containing layer into said skin until said skin is saturated with medicament; and (b) reversing said first polarity to stabilize said medicament within said skin for a second period of time of sufficient duration to permit at least partial depletion of said medicament within said skin.

* * * * *

UNITED STATES PATENT AND TRADEMARK OFFICE
CERTIFICATE OF CORRECTION

PATENT NO. : 5,415,629
DATED : May 16, 1995
INVENTOR(S) : Julian L. Henley

It is certified that error appears in the above-indentified patent and that said Letters Patent is hereby corrected as shown below:

Column 10, Line 64, kindly delete "sand" and insert --and-- therefor.

Signed and Sealed this

Twenty-eighth Day of April, 1998

Attest:

BRUCE LEHMAN

*Attesting Officer*    *Commissioner of Patents and Trademarks*